(12) United States Patent
Waltman

(10) Patent No.: US 6,839,590 B2
(45) Date of Patent: Jan. 4, 2005

(54) AVERAGE CURRENT MODE CONTROLLED ENERGY STORAGE IN A DEFIBRILLATOR

(75) Inventor: Barry F. Waltman, Brier, WA (US)

(73) Assignee: Medtronic Physio-Control Corp., Redmond, WA (US)

( * ) Notice: Subject to any disclaimer, the term of this patent is extended or adjusted under 35 U.S.C. 154(b) by 289 days.

(21) Appl. No.: 10/016,586

(22) Filed: Oct. 22, 2001

(65) Prior Publication Data

US 2003/0078620 A1 Apr. 24, 2003

(51) Int. Cl.⁷ .................................................. A61N 1/39
(52) U.S. Cl. .............................................................. 607/5
(58) Field of Search ............................................ 607/4–7

(56) References Cited

U.S. PATENT DOCUMENTS

| | | |
|---|---|---|
| 4,047,052 A | 9/1977 | Koubek et al. |
| 4,047,096 A | 9/1977 | Madewell |
| 4,070,699 A | 1/1978 | Einbinder |
| 4,075,536 A | 2/1978 | Stevens |
| 4,104,714 A | 8/1978 | Smith et al. |
| 4,394,583 A | 7/1983 | Standing |
| 4,489,369 A | 12/1984 | Ginsberg |
| 4,548,209 A | 10/1985 | Wielders et al. |
| 4,733,153 A | 3/1988 | Katzenstein |
| 4,985,821 A | 1/1991 | Cohen |
| 5,021,937 A | 6/1991 | Cohen |
| 5,291,382 A | 3/1994 | Cohen |
| 5,366,484 A | 11/1994 | Kroll |
| 5,438,505 A | 8/1995 | Cohen |
| 5,447,522 A * | 9/1995 | Chang et al. ................... 607/7 |
| 5,464,432 A | 11/1995 | Infinger et al. |
| 5,485,361 A * | 1/1996 | Sokal ....................... 363/21.17 |
| 5,488,553 A | 1/1996 | Renger |
| 5,554,925 A | 9/1996 | Shibata |
| 5,723,969 A | 3/1998 | Archer et al. |
| 5,800,461 A | 9/1998 | Menken et al. |
| 5,895,983 A | 4/1999 | Motomura |
| 5,899,923 A | 5/1999 | Kroll |
| 5,999,852 A | 12/1999 | Elabbady et al. |
| 6,005,370 A * | 12/1999 | Gustavson et al. ......... 320/137 |
| 6,101,111 A | 8/2000 | Blair |
| 6,147,460 A | 11/2000 | Ichihara |
| 6,240,112 B1 | 5/2001 | Partlo et al. |
| 6,243,604 B1 | 6/2001 | Garrett |

FOREIGN PATENT DOCUMENTS

| | | |
|---|---|---|
| DE | 118 009 | 2/1976 |
| GB | 1 551 728 | 8/1979 |
| GB | 2 153 164 | 8/1985 |
| JP | 57-202697 | 12/1982 |
| JP | 6-205253 | 7/1994 |
| JP | 10-161755 | 6/1998 |
| JP | 10-257767 | 9/1998 |
| JP | 2000-134923 | 5/2000 |
| JP | 2000-308342 | 11/2000 |
| SU | 515 218 | 5/1976 |
| SU | 517 976 | 6/1976 |
| SU | 570 955 | 8/1977 |
| SU | 692 919 | 10/1979 |
| SU | 1 417 129 | 8/1988 |
| WO | WO 00/04612 | 1/2000 |

* cited by examiner

Primary Examiner—Angela D. Sykes
Assistant Examiner—Roderick Bradford
(74) Attorney, Agent, or Firm—Shumaker & Sieffert, P.A.

(57) ABSTRACT

Techniques are described for charging an energy storage device, such as the high-voltage energy storage capacitors of an external defibrillation device, using an average current mode control technique. By controlling the average current in a transformer, energy may be stored rapidly and at controlled energy levels.

9 Claims, 4 Drawing Sheets

AVERAGE CURRENT MODE CONTROLLED ENERGY STORAGE IN A DEFIBRILLATOR

TECHNICAL FIELD

The invention relates generally to energy storage techniques for medical devices, and more particularly techniques employing switching-mode devices to store energy in an energy storage device associated with a defibrillator.

BACKGROUND

Many devices rely on an energy storage device such as a capacitor to store potential energy and supply a voltage to a load. Examples of such devices include photographic flash lamps and flashing warning lights.

A defibrillator is another device that stores energy, typically in one or more high-voltage capacitors, and delivers the stored energy to a patient. In particular, a defibrillator delivers energy to a heart that is undergoing fibrillation and has lost its ability to contract. Ventricular fibrillation is particularly life threatening because activity within the ventricles of the heart is so uncoordinated that virtually no pumping of blood takes place. An electrical pulse delivered to a fibrillating heart may repolarize the heart and cause it to reestablish a normal sinus rhythm.

Although defibrillators may be internally implanted in patients that suffer from chronic fibrillation, an electric pulse may also be applied externally via paddles placed upon the patient's chest. When a switch is closed, the capacitor sends at least a part of the stored energy from paddle to paddle through the patient's chest. The energy transferred may be on the order of several hundred joules. To achieve this level of energy transfer, the power needed to deliver the energy may be on the order of hundreds of kilowatts and the voltage across the capacitor may be on the order of several thousand volts.

A defibrillator such as a portable defibrillator typically includes a battery, which by itself is not capable of providing the high energy, high-voltage electric pulses required for defibrillation therapy. Instead, the battery is used to charge the high-voltage energy storage capacitors. In a flyback charger, the battery supplies energy to the primary coil of a flyback transformer while a control switch is closed. When the control switch is opened, the energy stored in the primary coil is transferred to the secondary coil of the flyback transformer. The energy is then stored on the storage capacitors, which are coupled to the secondary coil by a diode. By opening and closing the control switch, energy is incrementally transferred from the battery to the capacitors, thereby increasing the energy stored in the capacitors and charging the capacitors to a high voltage.

SUMMARY

The invention relates to techniques for charging an energy storage device, such as the high-voltage energy storage capacitors of an external defibrillation device, using average current mode control techniques. The time needed to charge a capacitor to a desired voltage is a function of the current flowing to the capacitor. By controlling the average current, the charge time and the voltage across the capacitor can be more effectively controlled.

Average current mode control represents a highly accurate technique for controlling current in a transformer, and consequently represents a highly accurate technique for storing energy in a storage element such as a capacitor in a short time. In devices such as a defibrillator, rapid and accurate energy storage are especially advantageous. The technique may be extended to a wide range of current levels, charge times and voltage levels.

In one embodiment, the invention is directed to a method for charging an energy storage device associated with a defibrillator. The method comprises applying current to a primary coil in a flyback transformer, sensing an average current through the flyback transformer, controlling the applied current to cause the average current to follow a reference current and transferring energy from the flyback transformer to an energy storage device. By controlling the applied current, the average current may be driven to follow a reference current. The reference current may be a function of one or more parameters, such as energy stored in the energy storage device. When the energy storage device is a capacitor, the stored energy is related to the voltage across the capacitor.

Average current mode control represents an accurate and versatile technique for storing energy in a storage element. By controlling average current, it is possible to control, for example, the time needed to charge a capacitor to a desired voltage level.

In another embodiment, the invention presents a device comprising an energy source and a charging circuit. The device charges an energy storage device associated with a defibrillator. The charging circuit transfers energy from the energy source to an energy storage device, such as a capacitor. The charging circuit includes a flyback transformer, and transfers energy as a function of the average current in the flyback transformer. The device may further comprise electrodes for delivering a defibrillation pulse to a patient and a switch that couples the electrodes to the energy storage device to deliver the defibrillation pulse to the patient.

In an additional embodiment, the invention presents a medical device comprising a transformer, an energy source that supplies energy to the primary coil of the transformer, a switch that regulates the supply of energy to the primary coil, an energy storage device that receives energy from the secondary coil of the transformer and a controller that controls the switch as a function of the average current in the transformer.

In a further embodiment, the invention presents a medical device comprising a difference circuit that generates an error signal as a function of the difference between a reference current and an average current in a transformer that transfers energy to an energy storage device. The device further includes a modulator that modulates the duty cycle of a control signal as a function of the error signal and a switch that regulates the supply of energy to a primary coil of the transformer according to the control signal. The control signal may have a constant period, which advantageously allows for management of the noise spectrum due to the control signal.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
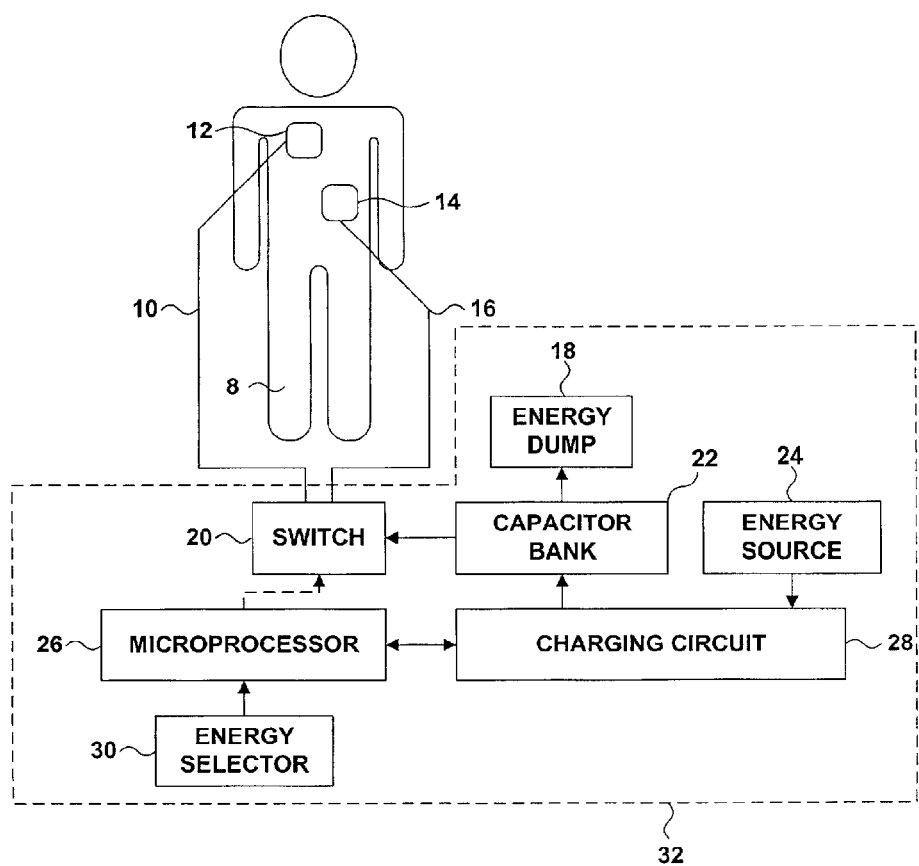
FIG. 1 is a block diagram illustrating components of a defibrillator.

FIG. 1 is a block diagram illustrating components of a defibrillator 32 formed in accordance with the present invention. Defibrillator 32 administers therapy to patient 8 via electrodes 12 and 14, which may be hand-held electrode paddles or adhesive electrode pads placed on the skin of patient 8. The body of patient 8 provides an electrical path between electrodes 12 and 14.

Patient electrodes 12 and 14 are coupled to switch 20 via conductors 10 and 16. Switch 20 couples patient electrodes 12 and 14 to the output of capacitor bank 22. Switch 20 is of conventional design and may be formed, for example, of electrically operated relays. Alternatively, switch 20 may comprise an arrangement of solid-state devices such as silicon-controlled rectifiers or insulated gate bipolar transistors. In each case, switch 20 should be capable of carrying relatively high currents.

Capacitor bank 28 stores the energy to be delivered to patient 8. The amount of energy to be delivered may be specified by an operator via energy selector 30. Energy selector 30 supplies energy-setting information to microprocessor 26 and controls the defibrillation pulse energy to be delivered to patient 8. Energy selector 30 can be set to a specific energy level by an operator, or may be set to one of a series of discrete energy levels. Defibrillator 32 may present energy selector 30 a part of a user interface which may take the form of one or more dials or switches and an interactive graphic or text display. In the case of an automated external defibrillator with preprogrammed energy levels, energy selector 30 may be eliminated.

Before a defibrillation pulse may be delivered to patient 8, capacitor bank 28 must be charged. Microprocessor 26 directs charging circuit 28 to charge capacitor bank 22 to a high voltage level. Charging circuit 28 delivers energy from energy source 24 to capacitor bank 22. As capacitor bank 22 stores energy, the voltage across capacitor bank 22 increases, up to a desired level. Energy source 24 may be, for example, a series of batteries or a regulated dc source powered by an ac line.

The desired level of voltage across capacitor bank 22 is a function of the energy to be delivered to patient 8. The energy to be delivered is in turn a function of factors such as the energy level selected with energy selector 30 and the impedance of the body of patient 8. Defibrillator 32 may include instrumentation (not shown in FIG. 1) to measure or estimate the impedance of the body of patient 8. Because the energy to be delivered to patient 8 is a function of the voltage across capacitor bank 22, the voltage across capacitor bank 22 is controlled. As will be described below, average current mode control of a flyback charging circuit is used to quickly charge capacitor bank 22 to the desired level.

When the voltage across capacitor bank 22 reaches the desired level, microprocessor 26 may activate switch 20 to electrically connect capacitor bank 22 to patient electrodes 12 and 14, and thereby deliver a defibrillation pulse to patient 8. Alternatively, microprocessor 26 may illuminate a light or activate another indicator that informs the operator that the defibrillator is ready to deliver a defibrillation pulse to patient 8. The operator may activate switch 20 and thereby deliver a defibrillation pulse to patient 8.

Before the pulse is administered, an audible warning of the impending pulse is ordinarily given so that no one other than patient 8 will receive the defibrillation pulse. The warning may be given by the operator, for example, to admonish others to discontinue physical contact with patient 8. In the case of an automated external defibrillator, the warning may be an audible alert sounded by defibrillator 32.

Activation of switch 20 closes a circuit in which patient 8 is a part. Switch 20 may control whether defibrillation is monophasic or biphasic. The goal of defibrillation is to repolarize the heart with the current and cause the heart to reestablish a normal sinus rhythm. In some patients, one defibrillation treatment is insufficient and one or more additional defibrillation pulses may be administered. Between pulses, capacitor bank 22 must recharge to a high energy level.

In recharging capacitor bank 22, as in the initial charging, time is usually of the essence. Charging circuit 28 should charge capacitor bank 22 efficiently, quickly and accurately to a controlled voltage. Charging circuit 28 may satisfy these objectives using average current mode control of a flyback charging circuit, in accordance with the invention.

In some circumstances, energy stored in capacitor bank 22 is not to be used to administer a defibrillation pulse. For example, the patient may recover normal sinus rhythm and may not need another shock. In circumstances such as this, the energy in capacitor bank 22 may be discharged with energy dump 18. Energy dump 18 may include resistive elements that receive energy from capacitor bank 22 and dissipate the energy as heat. Although energy dump 18 is shown separate from switch 20, some applications combine the functions of switch and energy dump.

Figure 2:
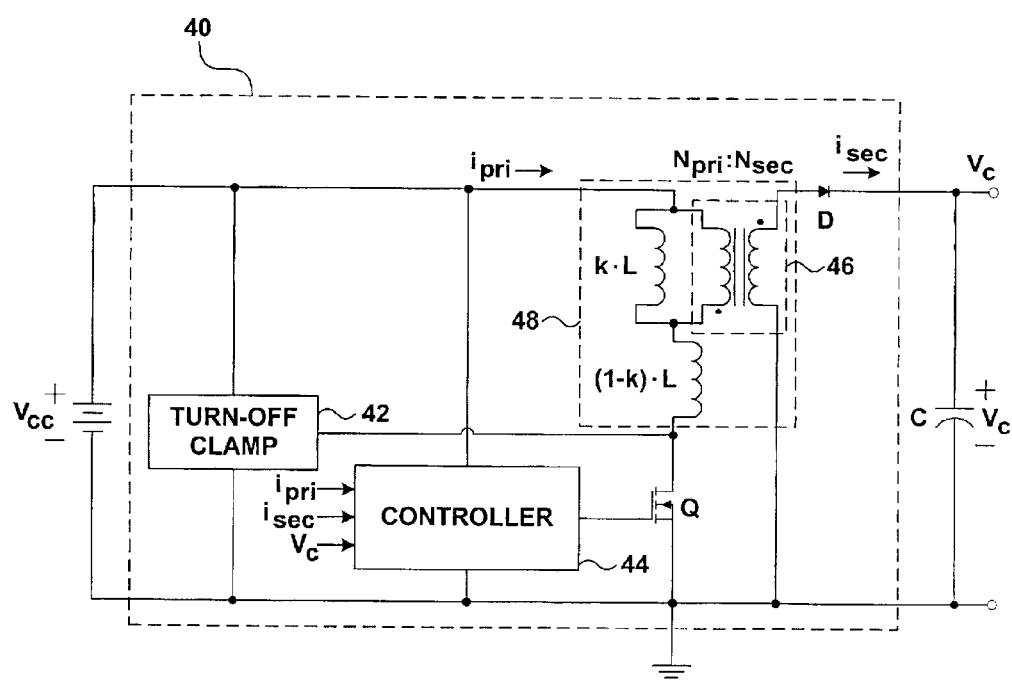
FIG. 2 is a circuit diagram of a power supply, charging circuit and energy storage device for use with a defibrillator as shown in FIG. 1.

FIG. 2 is a block diagram illustrating a flyback charging circuit 40 in cooperation with a capacitor bank, represented by energy-storage capacitor C. Charging circuit 40 delivers energy from an energy source, represented by battery $V_{cc}$, to capacitor C. As more energy is delivered to energy-storage capacitor C, the potential difference $V_c$ across energy-storage capacitor C increases.

Energy is delivered from battery $V_{cc}$ to energy-storage capacitor C via transformer 48. Transformer 48 is modeled as ideal transformer 46, with non-ideal characteristics modeled as additional coils on the primary side. The one additional coil represents the coupling of the primary and secondary coils with coupling coefficient k times inductance L, or k·L. The other coil models the transformer leakage inductance (1−k)·L. Ideally, k=1 and the primary and secondary coils have unity coupling.

Transformer 48 includes a primary coil, having $N_{pri}$ turns, and a secondary coil, having $N_{sec}$ turns. Current $i_{pri}$ is supplied by source $V_{cc}$, flows through the primary coil and induces current in the secondary coil. The current flowing through the secondary coil is $i_{sec}$.

Current flow is controlled by a switch, modeled as n-channel enhancement MOSFET Q. The state of transistor Q is governed by controller 44. When controller 44 turns transistor Q on, $i_{pri}$ flows into the primary coil of transistor 48, causing energy to be stored in the primary coil. When controller 44 turns transistor Q off, the energy stored in the primary coil transfers to the secondary coil, generating current $i_{sec}$. Current $i_{sec}$ flows through diode D and charges energy-storage capacitor C. Diode D prevents energy-storage capacitor C from discharging.

By turning transistor Q on and off, controller 44 supplies a series of current pulses to energy-storage capacitor C, thereby charging energy-storage capacitor C. Because of the non-ideal characteristics of transformer 48, a drain voltage spike may occur when controller turns off transistor Q. This voltage spike, which may affect the performance of transistor Q, is constrained by turn-off clamp circuit 42.

Energy-storage capacitor C is charged with a series of pulses. For optimal charging, however, the pulses are not of equal duration. As shown in FIG. 2, controller receives feedback and turns transistor Q on and off as a function of currents $i_{pri}$ and $i_{sec}$. Currents $i_{pri}$ and $i_{sec}$, which may be sensed by current sensors (not shown in FIG. 2) and fed back to controller 44, are parameters used in average current mode control. In addition, controller 44 may use the potential difference $V_c$ across energy-storage capacitor C as a feedback parameter.

Figure 3:
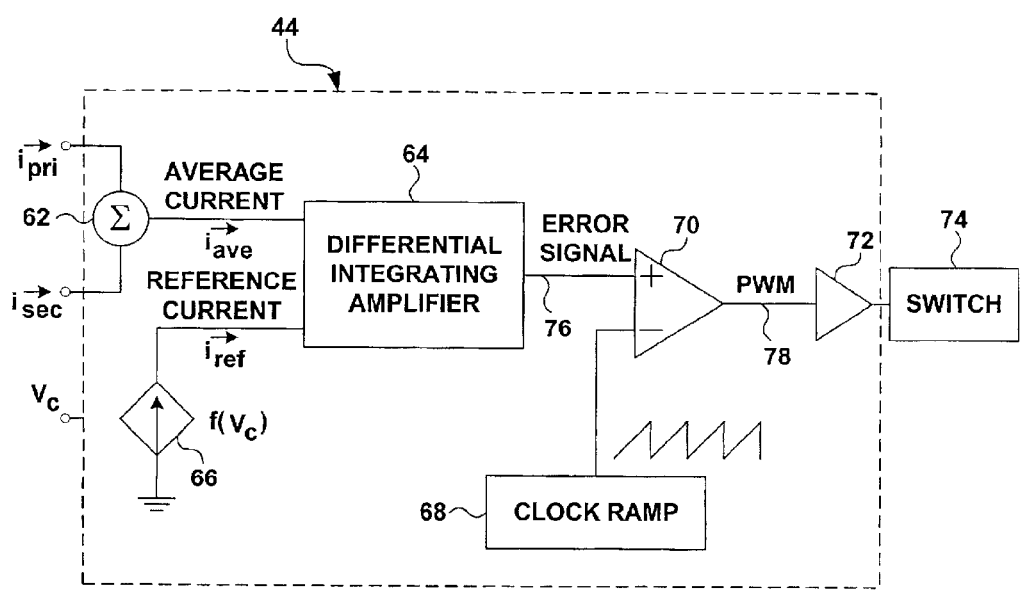
FIG. 3 is a circuit diagram illustrating a controller for average current mode control of the charging circuit of FIG. 2.

FIG. 3 is a block diagram of controller 44. Controller 44 receives currents $i_{pri}$ and $i_{sec}$ and provides a summer 62 that sums $i_{pri}$ and $i_{sec}$, generating current $i_{ave}$. Current $i_{ave}$ is the average current through transformer 48 and is, by definition, the sum of $i_{pri}$ and $i_{sec}$. Controller 44 activates switch 74 to drive $i_{ave}$ to follow a reference current, $i_{ref}$.

In a typical application, reference current $i_{ref}$ is a time-varying current and not a constant current. In the embodiment shown in FIG. 3, $i_{ref}$ depends upon the voltage $V_c$, but $i_{ref}$ may depend upon parameters other than or in addition to $V_c$. For example, $i_{ref}$ may vary as a function of supply voltage $V_{cc}$, to manage power and charge time. A current source 66 may be embodied as a processor that generates $i_{ref}$, or controls a variable current source that generates $i_{ref}$, as a function of the parameters.

The time needed to charge capacitor C to the desired level of voltage is a function of the charging current, which in turn is a function of $i_{ave}$. By controlling average current $i_{ave}$, therefore, controller 44 may quickly and efficiently charge capacitor C.

Average current $i_{ave}$ and reference current $i_{ref}$ are supplied to differential integrating amplifier 64, which generates error signal 76 as a function of the difference between average current $i_{ave}$ and reference current $i_{ref}$. Amplifier 64 typically comprises a control feedback loop to perform the differencing function. Amplifier 64 may also include integrating elements, i.e., reactive elements, that compensate the control loop. In addition, amplifier 64 may amplify the difference between average current $i_{ave}$ and reference current $i_{ref}$.

Error signal 76 may be a voltage signal or a current signal. As shown in FIG. 3, error signal 76 is a voltage signal, which is supplied as one input to comparator 70. The other input to comparator 70 is a clock signal such as periodic ramp signal 68. Clock ramp signal 68 has a fixed period, and therefore a fixed frequency. An advantage of having a fixed frequency for clock ramp signal 68 is that clock ramp signal 68 has a known noise spectrum. Consequently, the adverse effect of noise due to clock ramp signal 68 can be managed, such as by attenuating the noise with a filter or by generating signals at different frequencies to avoid interference with the noise spectrum of clock ramp signal 68.

The output of comparator 70 is a pulse-width modulated (PWM) signal 78. Information is encoded within PWM signal 78 in the duration of the pulses, rather than in the amplitude of the pulses. When the magnitude of error signal 76 is higher than clock ramp signal 68, the output of comparator 70 is a logically high voltage value such as 3V Otherwise, the output of comparator 70 is a logically low voltage value such as ground potential. When the magnitude of error signal 76 is larger, the duration of the high voltage pulse generated by comparator 70 is longer. Similarly, when the magnitude of error signal 76 is smaller, the duration of the high voltage pulse generated by comparator 70 is shorter. In this way, the duty cycle of PWM signal 78 varies according to error signal 76, but the period of PWM signal 78 remains constant.

PWM signal 78 opens and closes switch 74. Switch 74 may be, for example, a field effect transistor such as n-channel enhancement mode transistor Q in FIG. 2. Switch may also be any of a number of other electronic switches. Driver 72 drives switch 74. Depending on the kind of electronic switch being driven, driver 72 may, for example, amplify, invert, or clamp PWM signal 78 to drive switch 74.

Figure 4:
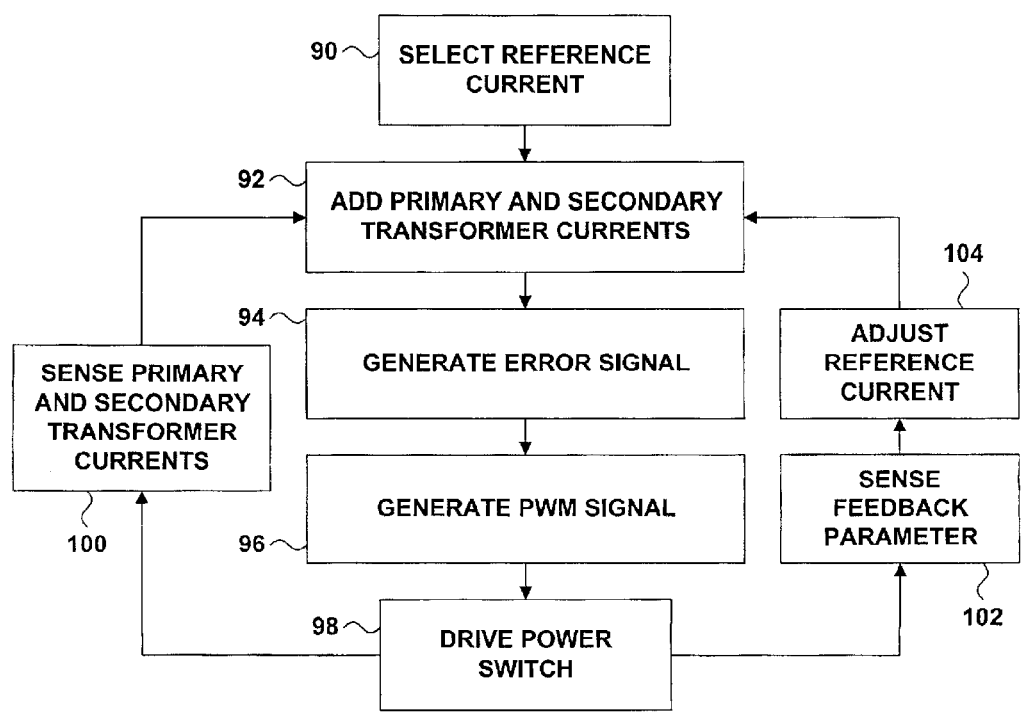
FIG. 4 is a flow diagram illustrating techniques for storing energy using average current mode control.

FIG. 4 is a flow diagram illustrating an embodiment of the invention. Charging begins with selection of an initial reference current $i_{ref}$ (90), to which controller 44 will drive average current $i_{ave}$. As mentioned above, reference current $i_{ref}$ ordinarily varies with time and may depend upon one or a combination of parameters.

Average current $i_{ave}$ is, by definition, the sum of primary current $i_{pri}$ and secondary current $i_{sec}$ so $i_{pri}$ and $i_{sec}$ are summed to produce $i_{ave}$ (92). Current sensors sense $i_{pri}$ and $i_{sec}$, which may be fed back to controller 44 as currents, and may be summed by application of Kirchhoff's current law. Alternatively, current sensors may sense $i_{pri}$ and $i_{sec}$ and convert the currents to voltages, which may be added with the sum being representative of $i_{ave}$.

Amplifier 64 takes the difference between average current $i_{ave}$ and reference current $i_{ref}$ and generates an error signal as a function of the difference (94). Comparator 70 compares error signal 76 to clock ramp signal 68 and generates PWM signal 78 as a function of the comparison (96). Driver 72 drives switch 74 as a function of PWM signal 78 (98).

As driver 72 drives switch 74, $i_{ave}$ changes to follow $i_{ref}$. Accordingly, $i_{pri}$ and $i_{sec}$ change as well. Current sensors sense $i_{pri}$ and $i_{sec}$, which are fed back to controller 44 (100) and are summed to produce $i_{ave}$ (92). Through feedback, $i_{ave}$ is driven to follow $i_{ref}$.

Reference current $i_{ref}$ may change as a function of one or more feedback parameters. Voltage $V_c$ and/or supply voltage $V_{cc}$, for example, may be sensed (102) and fed back to controller 44. Reference current $i_{ref}$ may be adjusted as a function of the feedback parameter (104) and may also be adjusted as a function of other parameters.

The invention offers several advantages. Average current mode control represents a highly accurate technique for controlling current in a transformer, and consequently represents a highly accurate technique for storing energy in a storage element such as a capacitor. The accuracy extends over a wide range of current levels, and consequently, the accuracy extends over a wide range of charge times and voltage levels. In addition, the transformer may operate in a continuous mode, in which current in transformer 48 is nonzero, or a discontinuous mode, in which current in transformer 48 may reach zero. The average current may be accurately controlled in either mode. Average current control mode using a clock signal with a fixed frequency offers the additional advantage of having a known, and therefore manageable, noise spectrum.

Various embodiments of the invention have been described. These embodiments are illustrative of the practice of the invention. Although described in detail in connection with a defibrillator, the invention may find application with other devices that store energy. The invention is not limited to eternal defibrillators but may be applied to internal medical devices such as implantable cardioverters/defibrillators.

Various modifications to the apparatus or methods may be made without departing from the scope of the invention. For example, signals representative of currents such as $i_{pri}$, $i_{sec}$, $i_{ave}$ and $i_{ref}$ may be scaled, inverted, converted to voltages or converted to digital values. Clock ramp signal 68 need not be a ramp, but may be one of a number of other waveforms, such as a triangular wave. Switch 74 may be driven with a signal that is not a PWM signal. These and other embodiments are within the scope of the following claims.

What is claimed is:

1. A method for charging an energy storage device associated with a defibrillator, the method comprising:

applying current to a primary coil in a flyback transformer;

sensing an average current through the flyback transformer;

controlling the applied current to cause the average current to follow a reference current; and transferring energy from the flyback transformer to the energy storage device.

2. The method of claim 1, wherein controlling the applied current to cause the average current to follow a reference current comprises:

determining the difference between the average current and a reference current; and controlling the applied current as a function of the difference.

3. The method of claim 2, wherein controlling the applied current to cause the average current to follow a reference current further comprises:

generating an error signal as a function of the difference;

comparing the error signal to a time-varying clock signal;

generating a modulation signal as a function of the comparison; and controlling the applied current with the modulation signal.

4. The method of claim 1, wherein transferring energy to the energy storage device comprises charging a capacitor.

5. The method of claim 4, further comprising adjusting the reference current as a function of the voltage across the capacitor.

6. The method of claim 1, further comprising supplying the applied current from a voltage source.

7. The method of claim 6, further comprising adjusting the reference current as a function of the voltage across the voltage source.

8. The method of claim 1, wherein sensing an average current through a flyback transformer comprises:

sensing the current through the primary coil of the transformer; and sensing the current through a secondary coil of the transformer.

9. The method of claim 8, wherein sensing an average current through a flyback transformer further comprises summing the current through the primary coil and the current through the secondary coil.

* * * * *